United States Patent

Fontanille et al.

[11] Patent Number: 5,987,966
[45] Date of Patent: *Nov. 23, 1999

[54] DEVICE FOR MEASURING THE QUANTITY OF COAL IN A BALL GRINDER

[75] Inventors: Daniel Fontanille, Hermeray; Jacques Barbot, Clamart, both of France

[73] Assignee: GEC Alsthom Stein Industrie, Velizy-Villacoublay, France

[*] Notice: Under 35 U.S.C. 154(b), the term of this patent shall be extended for 155 days.

[21] Appl. No.: 08/494,078

[22] Filed: Jun. 23, 1995

[30] Foreign Application Priority Data

Jun. 24, 1994 [FR] France .................................. 94 07807

[51] Int. Cl.$^6$ ...................................................... G01N 9/00
[52] U.S. Cl. ................................ 73/32 A; 73/628; 73/649
[58] Field of Search .............................. 73/624, 630, 632, 73/597, 32 A, 628, 649

[56] References Cited

U.S. PATENT DOCUMENTS

| | | | |
|---|---|---|---|
| 3,834,233 | 9/1974 | Willis et al. | 73/290 V |
| 3,925,850 | 12/1975 | Lytton | 73/160 X |
| 3,984,895 | 10/1976 | Grice, Jr. | 73/32 A |
| 4,212,201 | 7/1980 | Hirsch et al. | 73/290 V |
| 4,399,701 | 8/1983 | Dunlop | 73/579 |
| 4,412,188 | 10/1983 | Zetting et al. | 340/558 |
| 4,624,129 | 11/1986 | Haynes . | |
| 4,909,449 | 3/1990 | Etheridge | 73/290 V X |
| 4,930,511 | 6/1990 | Rossman et al. | 128/661.03 |
| 5,105,661 | 4/1992 | Sekita et al. | 73/290 V |
| 5,280,724 | 1/1994 | Higo et al. | 73/624 |

FOREIGN PATENT DOCUMENTS

| | | | |
|---|---|---|---|
| WO 90/10849 | 9/1990 | European Pat. Off. | 73/290 V |
| 3412615A1 | 10/1985 | Germany . | |
| 4023179A1 | 1/1991 | Germany . | |
| 2054146 | 2/1981 | United Kingdom | 73/628 |
| 2160974 | 1/1986 | United Kingdom . | |

*Primary Examiner*—George Dombroske
*Assistant Examiner*—Paul D. Amrozowicz
*Attorney, Agent, or Firm*—Sughrue, Mion, Zinn Macpeak & Seas, PLLC

[57] ABSTRACT

A device for continuously measuring the quantity of coal inside a ball grinder including an ultrasound wave or electromagnetic wave emitter and a wave receiver. The emitter and the receiver are disposed so that the wave passes through at least part of the interior of the grinder. The receiver is associated with an electronic circuit for deducing the quantity of coal by comparing the signal received with data obtained from previous calibration measurements.

9 Claims, 3 Drawing Sheets

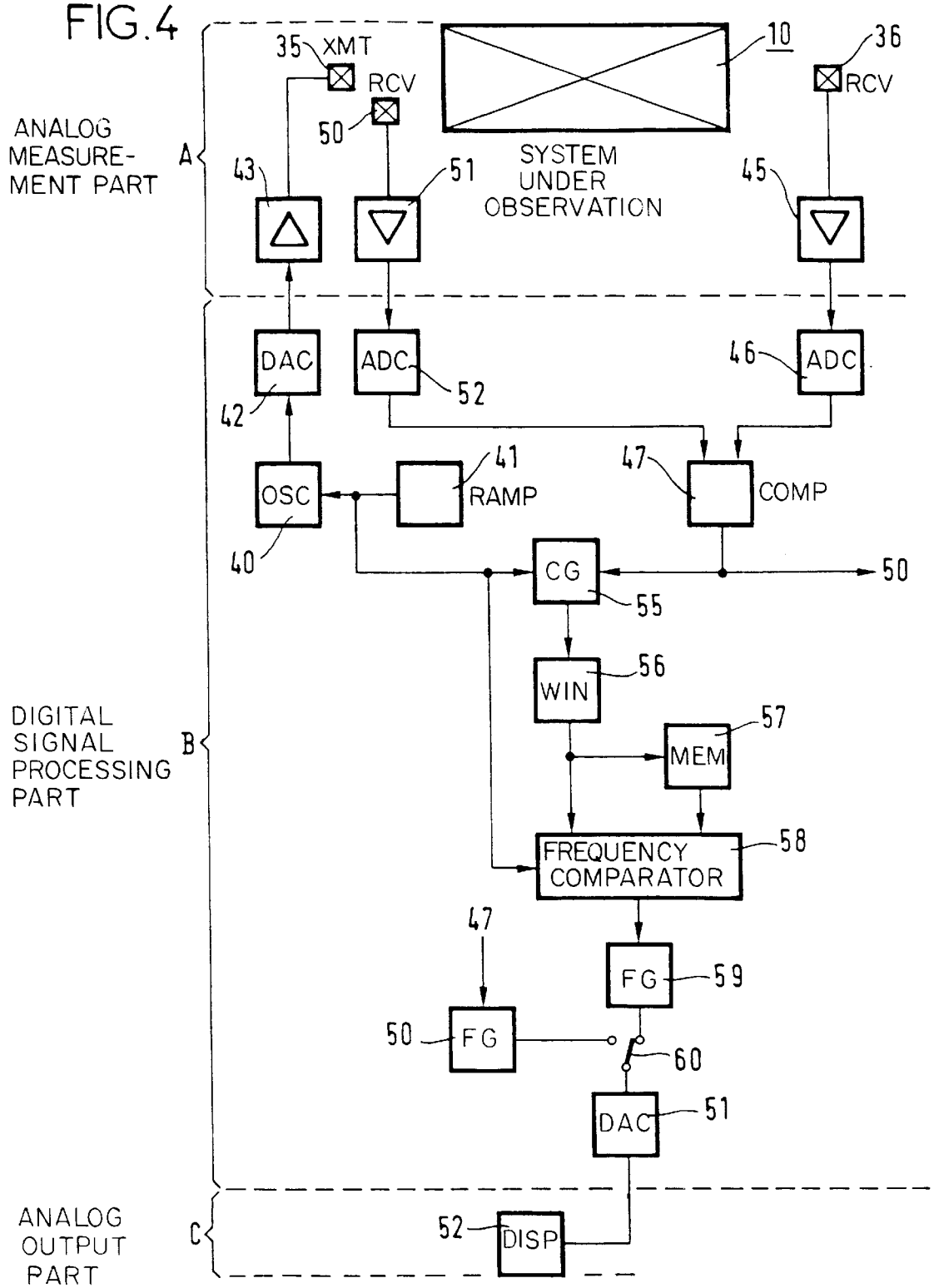

DEVICE FOR MEASURING THE QUANTITY OF COAL IN A BALL GRINDER

BACKGROUND OF THE INVENTION

1. Field of the Invention

The present invention relates to continuous measurement of the quantity of coal in a ball grinder.

2. Description of the Prior Art

When using a ball grinder, it is necessary to verify continuously that the quantity of coal is constant, to secure optimum grinding and optimum drying. If the quantity of coal introduced is too great, the grinding is insufficient and the drying is imperfect; if the quantity of coal introduced is too small, the downstream boiler receives insufficient feed.

Systems have been designed to estimate the quantity of coal contained in an operating ball grinder.

A first system is based on the variation in the measured power absorbed by the electric motor driving the ball grinder. This method is of low sensitivity; also, it requires frequent recalibration as the balls wear down or new balls are added.

Another system is based on the use of level sensors.

Pneumatic sensors each including a pneumatic hose with one end inside the grinder are used to measure the pressure difference between two levels; the quantity of coal in the grinder can be deduced from this measurement. However, the level sensors are installed in a hostile environment (coal dust, dropping balls, risk of clogging, etc) with the result that there is a high risk of failure; the sensors are connected to a complex and therefore costly pneumatic unit which is also costly to maintain. The availability of a system of this kind is only moderate.

A further system is based on measuring the noise emitted by the grinder. This method has the drawback of supplying a signal that is highly dependent on the throughput of the grinder, the size of the coal fragments introduced, the quantity of balls present in the grinder and the wear of the armor plating on the inside walls of the grinder.

One object of the present invention is to provide a device for measuring the quantity of coal in a grinder that is accurate, that does not require any equipment to be installed in the hostile environment inside the grinder, and the result of which does not depend on the particle size of the raw coal feed, the throughput of the grinder, the quantity of balls or the degree of wear of the balls.

Another object of the invention is to provide a low-cost high-availability measuring device.

A further object of the invention is to provide a device which can be recalibrated without intervention inside the grinder and without stopping operation of the grinder.

SUMMARY OF THE INVENTION

The invention consists in a device for continuously measuring the quantity of coal inside a ball grinder, comprising an ultrasound wave or electromagnetic wave emitter, a wave receiver, the emitter and the receiver being disposed so that the wave passes through at least part of the interior of the grinder, and an electronic circuit associated with the receiver for deducing the quantity of coal by comparing the signal received with data obtained from previous calibration measurements.

The measurement is based on a phenomenon selected from the group comprising wave absorption and wave speed variation.

The emitter is an ultrasound emitter and the receiver is an ultrasound receiver, the measurement being based on the amplitude difference between the signal emitted and the signal received.

The emitter is an ultrasound emitter and the receiver is an ultrasound receiver, the ultrasound emitter frequency being scanned in a given range of frequencies and the measurement being based on the difference between the measured frequency of the absorption peak and the frequency of the absorption peak in coal-free air.

The frequency range extends from 400 000 Hz to 1 MHz.

The emitter and the receiver are disposed on opposite sides of the grinder, on the rotation axis of the grinder, the wave travelling axially through the grinder.

The invention will be better understood from a reading of the following description of one specific embodiment of the invention given by way of non-limiting illustrative example only with reference to the appended drawings.

BRIEF DESCRIPTION OF THE DRAWINGS

FIG. 4 is a block diagram of an electronic circuit for implementing the measuring device of the invention.

DETAILED DESCRIPTION OF THE INVENTION

Figure 1:
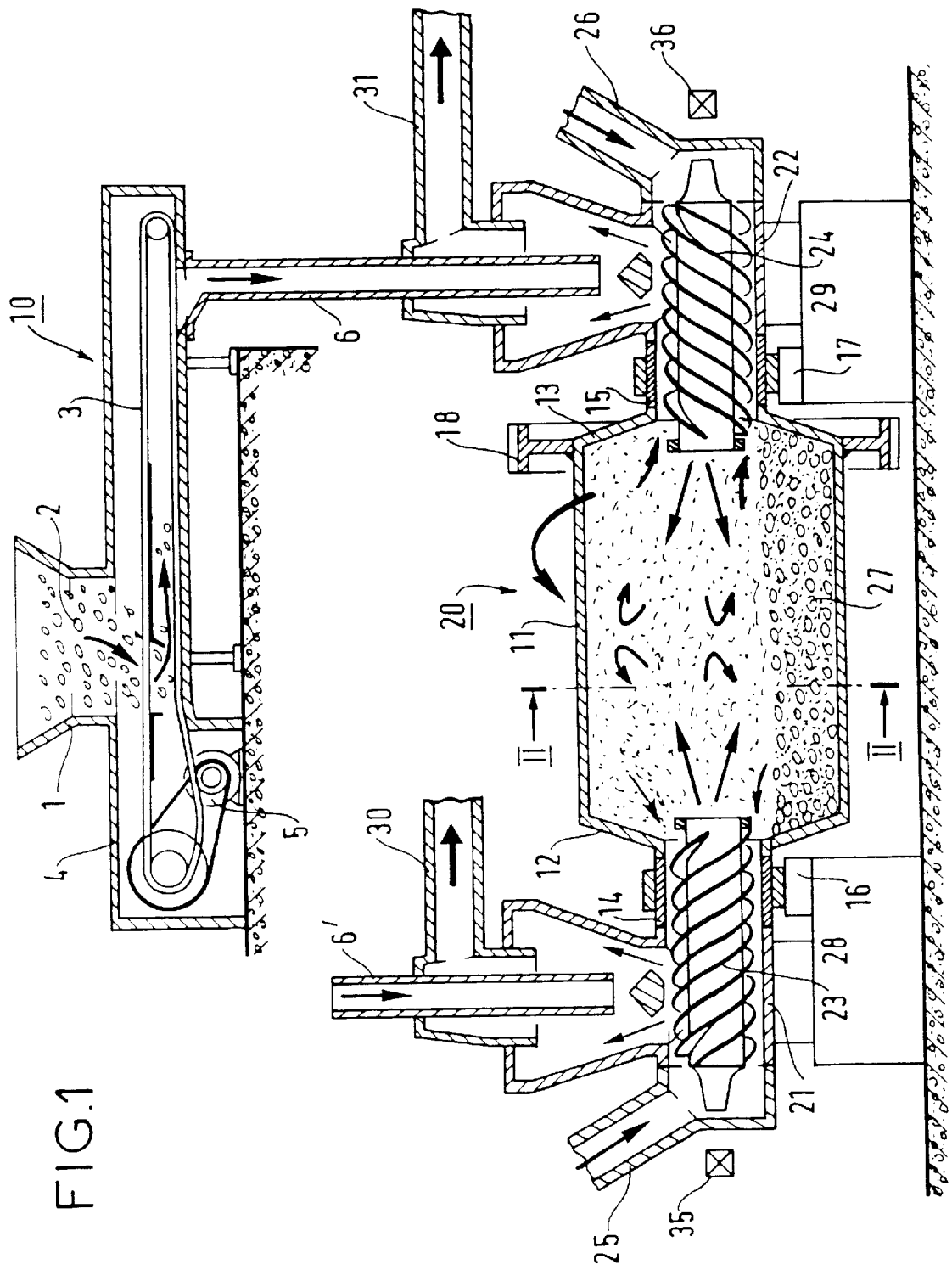
FIG. 1 is a diagrammatic view in elevation and section of a coal grinding installation equipped with a measuring device of the invention.

In the example described now and shown in FIG. 1, the grinder is a cylindrical grinder with an Archimedes screw feed. It is clear that the invention applies to any type of ball grinder (biconical grinders, for example) and regardless of the device for feeding coal into the grinder.

FIG. 1 is a diagram showing a coal grinding installation comprising at least one feed device 10 feeding coal to a ball grinder 20.

The feed device 10 comprises a storage hopper 1 from which coal 2 is extracted and fed by a chain conveyor 3 in a box 4 and driven by a motor 5 to a first end of a vertical pipe 6.

The grinder 20 comprises a cylinder 11 with two conical end portions 12 and 13 to which are fixed respective journals 14 and 15 adapted to support the cylinder. The journals are supported on respective bearings 16 and 17. The grinder is rotated by means of a toothed ring 18 cooperating with a gear (not shown) driven by an electric motor-gearbox (not shown).

Two tubular portions 21 and 22 coaxial with the journals 14 and 15 are provided with respective coaxial elastic Archimedes screws 23 and 24 and rotate with the grinder. Hot air is fed through respective pipes 25 and 26 into the interior of the tubular portions 21 and 22 at a pressure of a few tens of hectopascals. The coal is gravity fed through the pipe 6, the second end of which discharges in line with the tubular portion 22. Coal also reaches the other tubular portion 21 via a pipe 6' from another feed device (not shown). The coal is fed into the grinder by virtue of the rotation of the Archimedes screws 23 and 24.

The grinder is filled with balls 27, for example steel balls. When the cylinder rotates, the balls crush the coal; the fine particles of coal are entrained by the hot air into the annular spaces 28, 29 between the respective journals 14, 15 and the tubular portions 21, 22 and are taken off to the burners via pipes 30 and 31.

Figure 2:
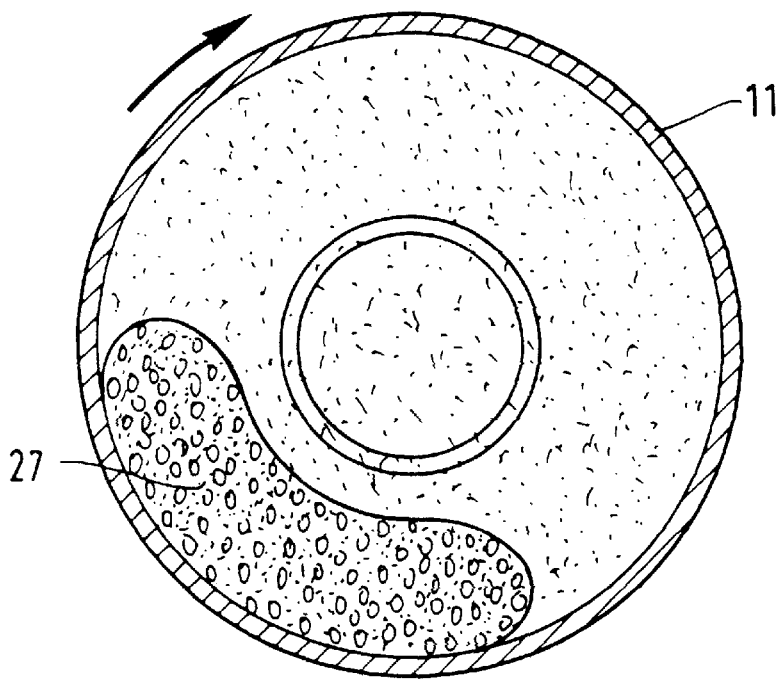
FIG. 2 is a view in section on the line II—II in FIG. 1.

FIG. 2 is an enlarged view in section of the cylinder when in operation. It shows the mass of balls 27 which is offset to one side because of the rotation of the cylinder in the direction of the arrow. The coal dust produced by the grinding lies on top of this mass.

In the example described, the device of the invention includes an ultrasound emitter 35 outside the grinder and emitting parallel to the rotation axis of the grinder, through the tubular portion 21; the ultrasound travels through the grinder and the tubular part 22 and is received by a receiver 36 outside the grinder, coaxial with the emitter. Holes are provided in the enclosure to enable passage of the ultrasound.

It has been observed that the presence of the coal dust causes attenuation of alternating transmission. There is a one-to-one relationship between the density of coal dust inside the grinder, and thus the quantity of coal introduced, and the attenuation of an incident wave. It is therefore sufficient to compare the amplitude of the wave received and the amplitude of the wave emitted to determine the quantity of coal inside the grinder.

The waves used can be of any type: sound waves, electromagnetic waves (including visible and invisible light waves, X-rays or Gamma-rays), etc.

The example described hereinafter relates to the use of ultrasound waves in a range of frequencies between 400 000 Hz and 1 MHz, for example.

To understand the invention it must be borne in mind (see FIG. 3) that the absorption A of a sound signal passing through a gaseous medium such as air is, in theory, directly proportional to the square of the frequency N of the wave, thus:

$A = K\ N^2$ where K is a constant.

Figure 3:
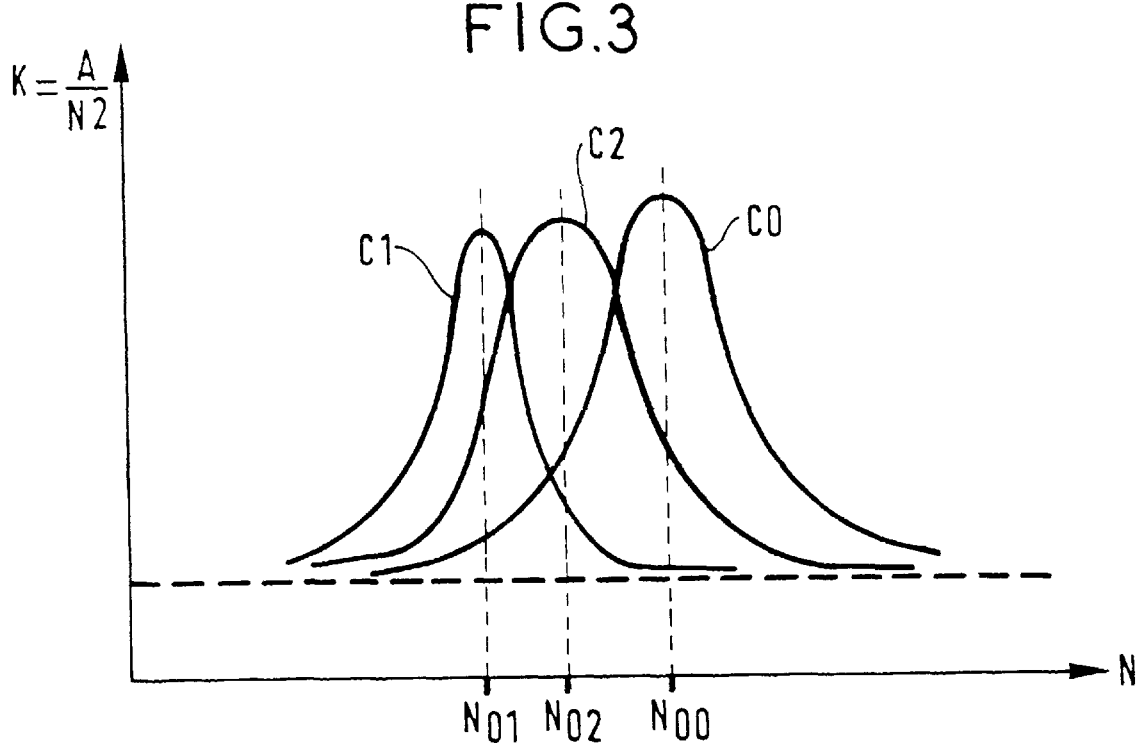
FIG. 3 is a diagram showing the variations in the theoretical value and in the actual value of the corrected absorption as a function of the frequency of a sound wave travelling through the grinder.

The diagram in FIG. 3 shows the theoretical value of A as a function of the frequency (dashed line curve). This is a straight line parallel to the abscissa axis.

In practice this coefficient K, also known as the corrected absorption, is not constant (invariant with frequency), but has a peak centred on a particular frequency No called the resonant frequency. If the gaseous medium, the air, for example, is loaded with particles in suspension, the value of No depends on the density of the particles in the gas.

A sound wave propagating in a gas has to be considered as a propagation of pressure waves in the medium. The gas molecules are agitated at a speed which is directly related to the frequency and can transfer some of their energy to the particles in suspension. There is elastic coupling between the air molecules and the particles, with a resonant frequency No dependent on the density of the particles.

FIG. 3 shows the variations in the absorption for three values of the density of particles in suspension.

The curve C0 is the absorption curve for a density d0=0 of particles (air free of particles). The resonant frequency is equal to $N_{00}$.

Curves C1 and C2 are absorption curves for two values d1 and d2 of density of particles of the same kind and with identical particle sizes. The resonant frequencies are respectively $N_{01}$ and $N_{02}$. Hereinafter, $N_{0n}$ refers to the resonant peak corresponding to a density dn of particles.

The circuit in FIG. 4 comprises an analog "measurement" part A, a digital measured signal processing part B and an analog output part C.

An ultrasound emitter 35 emits waves which pass through the device 10 to be observed, which is a gaseous medium (usually air) laden with particles in suspension and the density of which is to be measured.

The ultrasound emitter 35 is fed by a subsystem comprising a digital oscillator 40 the output frequency of which is varied in accordance with a sawtooth ramp signal produced by a ramp circuit 41. The output signal of the oscillator is converted to an analog signal by a digital-analog converter 42. After amplification by a power amplifier 43 it is applied to the ultrasound emitter 35.

The ultrasound wave is picked up by two receivers, a receiver 50 near the emitter 35 and a receiver 36 at the exit of the system 10 under observation. The signals are amplified by respective amplifiers 51 and 45 and then converted into digital signals by respective analog-digital converters 52 and 46; the converter 52 produces a reference signal Sr and the converter 46 produces a measurement signal Sm.

An amplitude comparator 47 supplies a measurement signal which represents the amplitude difference between the signals Sm and Sr. This difference is representative of the absorption of the sound wave in the medium under observation. A point by point curve generator 55 compiles this measured difference to establish a relationship between the corrected absorption $A/N_{0n}$ as a function of the frequency N in accordance with the characteristic curve Cn. A circuit 56 provides an observation window within this curve for determining the frequency of the peak corresponding to the absorption frequency.

The system is calibrated by measuring the absorption of the medium free of particles in suspension. This yields the frequency $N_{00}$ which is stored in a circuit 57.

During a measurement in the presence of particles in suspension, the resonant frequency $N_{0n}$ calculated by the circuit 56 is fed to a frequency comparator circuit 58 which receives from the circuit 57 the reference resonant frequency $N_{00}$.

The comparator 58 supplies an output signal representing the frequency offset $\Delta F = N_{0n} - N_{00}$ which is a direct function of the density of particles in suspension.

The signal $\Delta F$ is fed to a function generator 59 which delivers a signal that can be processed by amplification and linearization of the signal $\Delta F$. After conversion to an analog signal by a digital-analog converter 61, the signal is passed to a display 62 and if appropriate to an actuator (not shown) for automatically controlling the density of particles in suspension.

The output of the comparator 47 can be used directly as a measurement output during the calibration phase; the output signal of the comparator 47 is processed by a function generator 50 to obtain a suitable signal, which is then converted into an analog signal by the digital-analog converter 61. A switch 60 selects calibration or normal measurement.

The invention is not limited to the embodiment described and shown, which is given by way of example only.

In the example given, the wave passes through all of the grinder. As an alternative, the wave can pass through only part of the grinder, being reflected from an obstacle and collected and measured by a receiver on the same side of the grinder as the emitter.

In a different embodiment of the invention the phenomenon for characterizing the value of the density can be the wave velocity.

There is claimed:

1. Device for continuously measuring the quantity of coal inside a ball grinder, comprising an ultrasound wave or electromagnetic wave emitter, a wave receiver, the emitter and the receiver being disposed so that the wave passes through at least part of the interior of the grinder, and an electronic circuit associated with said receiver for deducing the quantity of coal by comparing the signal received with data obtained from previous calibration measurements, wherein the emitter and the receiver are disposed on opposite sides of the grinder, on a rotation axis of the grinder, the wave passing axially through the grinder.

2. Device according to claim 1 wherein the measurement is based on a phenomenon chosen from the group comprising absorption of the wave and variation of the speed of the wave.

3. Device according to claim 1 wherein the emitter is an ultrasound wave emitter and the receiver is an ultrasound wave receiver, the measurement being based on the amplitude difference between the signal emitted and the signal received.

4. Device according to claim 1 wherein the emitter is an ultrasound wave emitter and the receiver is an ultrasound wave receiver, the ultrasound wave emitter frequency being scanned in a given range of frequencies and the measurement being derived from the difference between the measured frequency of the absorption peak and the frequency of the absorption peak in air free of coal.

5. Device according to claim 4 wherein the frequency range extends from 400 000 Hz to 1 MHz.

6. Device according to claim 1 further comprising:

a wave emitter adapted to scan a given range of frequencies, a first wave receiver disposed near the wave emitter and supplying a reference receive signal, a second wave receiver disposed to receive the wave emitted by the emitter after it has passed through said grinder, and emitting a receive signal, a first comparator emitting a difference signal representative of the difference between the receive signals from the first and second receivers, a curve generator receiving the signal from the first comparator and producing the curve representative of the amplitude of said difference signal as a function of the frequency, a window calculator determining the frequency $N_{0n}$ of the resonant peak, and a second comparator producing a signal representing the frequency offset $\Delta F$ between the frequency $N_{0n}$ of the absorption resonant peak and a reference frequency $N_{00}$ produced by a measurement in the absence of particles and memorized.

7. Device according to claim 6 wherein the first comparator is a digital comparator receiving the signals from the first wave receiver and the second wave receiver after digitization by analog-digital converters.

8. Device according to claim 6 wherein the wave emitter is fed by an oscillator excited by a ramp circuit.

9. Device according to claim 6 wherein the signal representing the frequency offset $\Delta F$ is fed to a function generator which amplifies it and linearizes it.

* * * * *